US00PP34853P2

(12) United States Plant Patent
Berry

(10) Patent No.: US PP34,853 P2
(45) Date of Patent: Dec. 20, 2022

(54) ***LAGERSTROEMIA* PLANT NAMED 'JBG 19013'**

(50) Latin Name: *Lagerstroemia indica*
Varietal Denomination: 'JBG 19013'

(71) Applicant: Capstone Plants, Inc., Grand Saline, TX (US)

(72) Inventor: James Berry, Emory, TX (US)

(73) Assignee: CAPSTONE PLANTS, INC., Grand Saline, TX (US)

( * ) Notice: Subject to any disclaimer, the term of this patent is extended or adjusted under 35 U.S.C. 154(b) by 0 days.

(21) Appl. No.: 17/875,373

(22) Filed: Jul. 27, 2022

(51) Int. Cl.
*A01H 5/02* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 5/02
See application file for complete search history.

*Primary Examiner* — Kent L Bell
(74) *Attorney, Agent, or Firm* — Weatherly IP Solutions, LLC; Barbara Campbell

(57) ABSTRACT

A new cultivar of *Lagerstroemia* named 'JBG 19013' that is distinguishable by a compact dense shrub-like mounded plant habit, glossy green foliage and pink flowers borne in profusion and continually from early summer into fall. 'JBG 19013' is very well adapted to heat, humidity and drought conditions and exhibits slight or occasional susceptibility to aphids, whitefly and powdery mildew, is disclosed.

3 Drawing Sheets

Genus and species: *Lagerstroemia indica.*
Variety denomination: 'JBG 19013'.

BACKGROUND

The present disclosure relates to a new and distinct cultivar of *Lagerstroemia* plant, commonly known as Crape Myrtle, a shrub that is grown for use as an ornamental landscape and container plant. The new variety is known botanically as *Lagerstroemia indica* and will be referred to hereinafter by the cultivar name 'JBG 19013'.

'JBG 19013' originated as a selected seedling from a *Lagerstroemia* breeding program which was started in 2008. The breeding program was conducted at the inventor's nursery in Grand Saline, Tex. The aim of the breeding program is to develop new and improved genetics of green leafed Crape Myrtles which exhibit high degrees of pest and disease resistance, high flower counts and re-flowering periods. Varieties released from the breeding program are intended to be hardy, durable, and low maintenance for the consumer. 'JBG 19013' was selected in 2016 as a seedling from the open-pollination of the tree form of *Lagerstroemia* named 'Ruby Prince' (unpatented) the female parent, by an unknown, unnamed male parent (unpatented) plant within a proprietary collection of green-leafed *Lagerstroemia* varieties. 'JBG 19013' was selected for its exceptionally compact shrub-like form with attractive glossy green foliage, and profuse flowering which, at peak bloom, almost covers the foliage and which lasts into fall.

'JBG 19013' was first asexually propagated in 2017 in a greenhouse in a nursery in Grand Saline, Tex. using softwood cuttings. 'JBG 19013' has been confirmed to be stable and reproduces true to type in successive generations of asexual reproduction via softwood cuttings.

SUMMARY

The following traits have been repeatedly observed and represent the distinguishing characteristics of 'JBG 19013'.

'JBG 19013' has not been tested under all possible conditions and phenotypic differences may be observed with variations in environmental, climatic, and cultural conditions, without however, any variance in genotype.

1. 'JBG 19013' exhibits a compact dense shrub-like mounded plant habit.
2. The foliage of 'JBG 19013' is glossy and green in color.
3. Plants of 'JBG 19013' bear pink flowers in profusion and is in continual bloom, and re-blooms, from early summer into fall.
4. After one year's growth in a container, plants of 'JBG 19013' are 90 cm in height and 120 cm in width.
5. When established in the landscape, plants of 'JBG 19013' are 2 m in height and 2 m in width.
6. 'JBG 19013' is very well adapted to heat, humidity and drought conditions.
7. 'JBG 19013' exhibits slight or occasional susceptibility to aphids, whitefly and powdery mildew.

DESCRIPTION OF THE PHOTOGRAPHS

The accompanying color photographs illustrate the overall appearance of the new *Lagerstroemia* cultivar 'JBG 19013' showing the colors as true as it is reasonably possible to obtain in colored reproductions of this type. Photographs were taken in July 2022 in Grand Saline, Tex. from a fifteen-month-old plant grown outdoors in a 2-gallon container, with one pinch after initial cutting establishment and without any chemical growth regulators. Colors in the photographs may differ from the color values cited in the detailed botanical description, which accurately describes the actual colors of the new variety 'JBG 19013'.

DESCRIPTION OF THE NEW VARIETY

Figure 1:
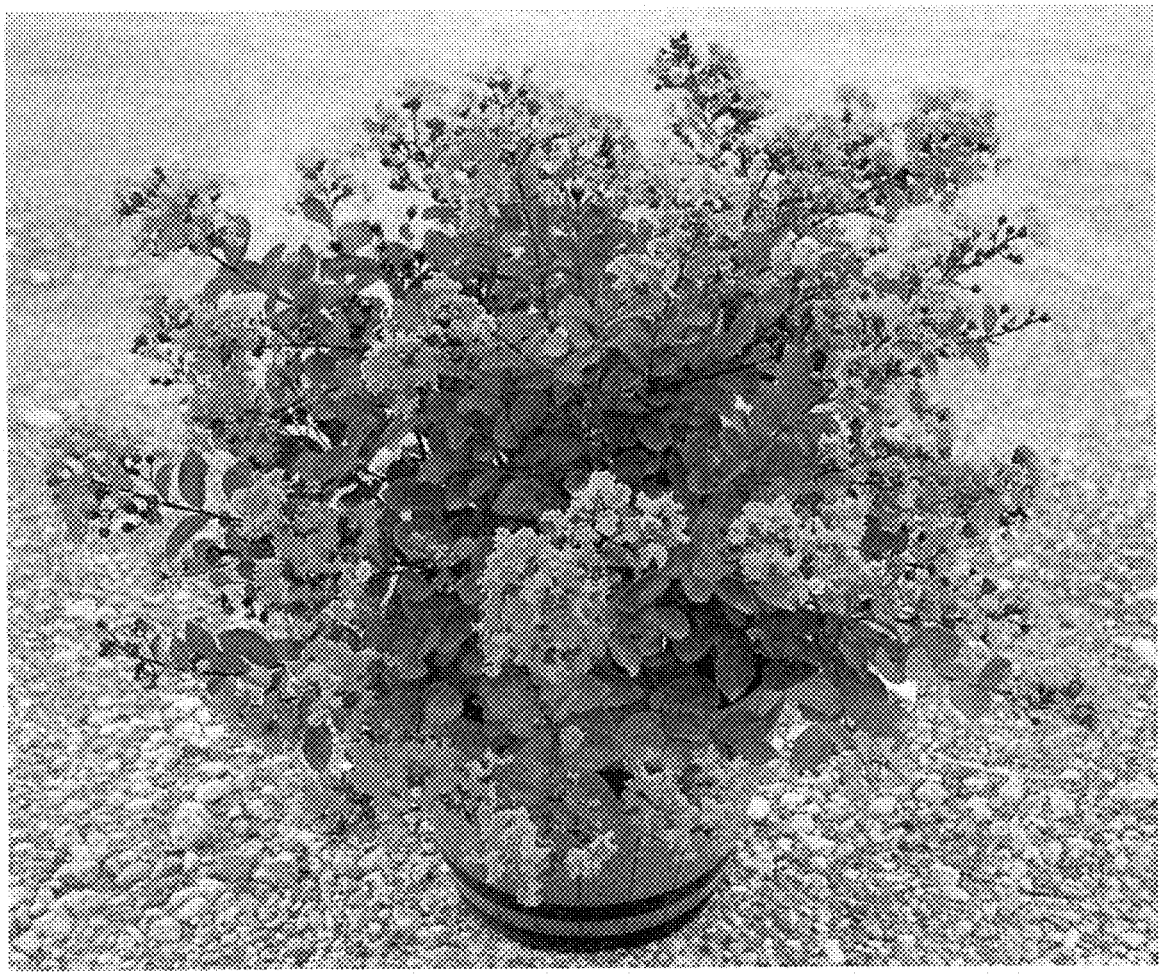
FIG. 1 depicts an entire plant in flower of 'JBG 19013'.
Figure 2:
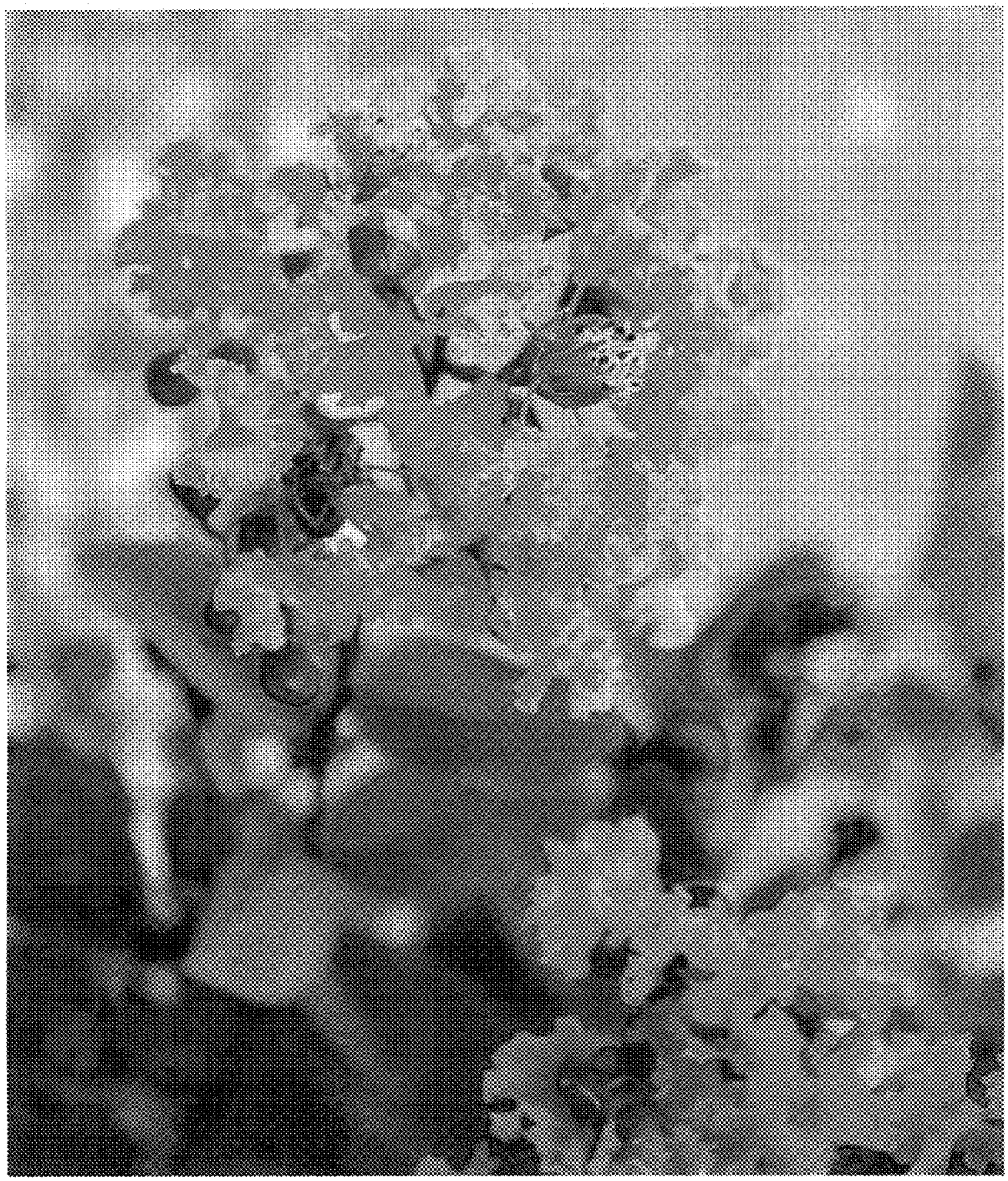
FIG. 2 depicts a close-up view of the inflorescence and flowers of 'JBG 19013'.
Figure 3:
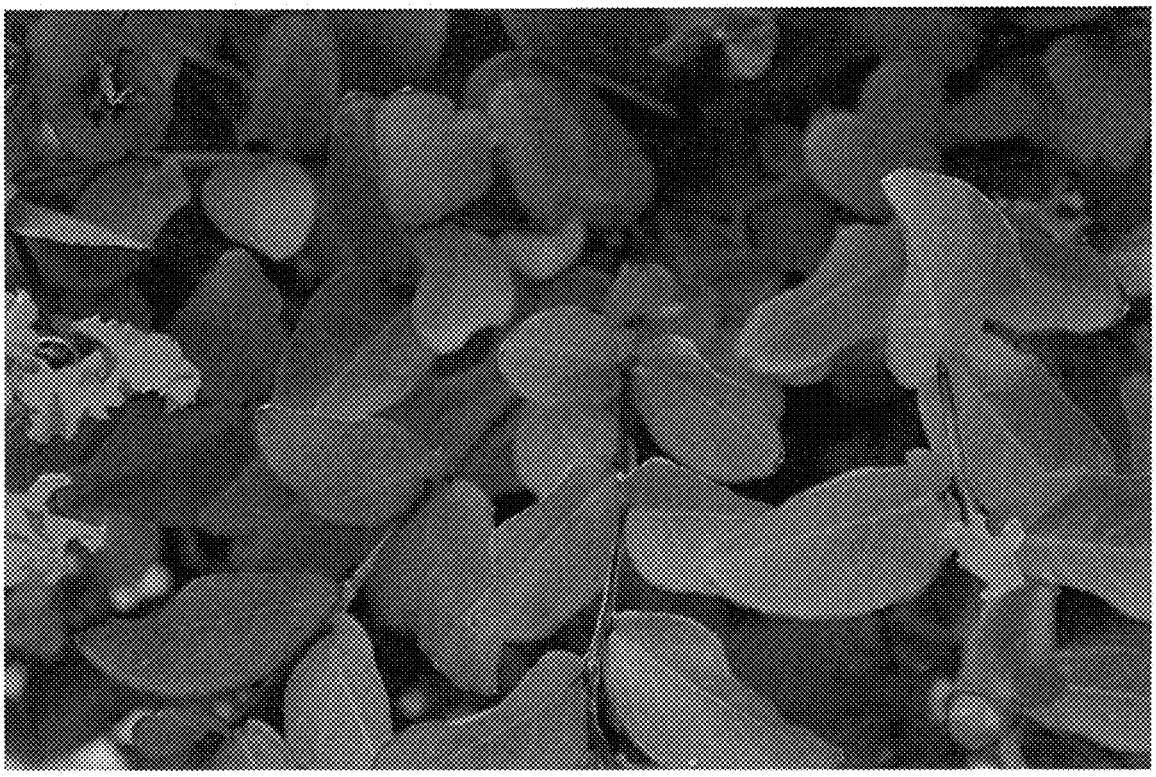
FIG. 3 depicts a close-up view of the foliage of 'JBG 19013'.

The following detailed descriptions set forth the distinctive characteristics of 'JBG 19013'. Observations, measurements, values, and comparisons were collected in July 2022 in Grand Saline, Tex. from a fifteen-month-old plant which was growing outdoors in full sun in a 2-gallon container. Color determinations were made in accordance with The 2007 Royal Horticultural Society Colour Chart from London England, except where general color terms of ordinary dictionary significance are used.

Classification:
- *Family.*—Lythraceae.
- *Genus.*—*Lagerstroemia.*
- *Species.*—*Indica.*
- *Common name.*—Crape Myrtle.

Parentage:
- *Female parent.*—*Lagerstroemia* 'Ruby Prince' (unpatented).
- *Male parent.*—Unknown.

Plant:
- *Propagation method.*—Softwood cuttings.
- *Rooting system.*—Fine and fibrous, white to light brown in color.
- *Vigor.*—Moderate vigor.
- *Time to develop roots.*—12 days are needed for a cutting to develop roots at recommended rooting temperature of 20° to 22° Centigrade.
- *Crop time.*—Approximately 10 to 12 months are required to produce a budded and flowering plant in a 2-gallon container. Larger containers require a longer period of growth in order to fill out. Flowering will continue from early summer and into fall.
- *Suggested container sizes.*—8-inch, 2-gallon, 7-gallon.
- *Use.*—Ornamental for use as a landscape plant or container plant.
- *Type.*—Flowering shrub.
- *Form.*—Mounded.
- *Growth habit.*—Dense, compact.
- *Overall dimensions.*—After one year's growth in a container, plants of 'JBG 19013' are 90 cm in height and 120 cm in width. When well established in the landscape, plants of 'JBG 19013' are 2 m in height and 2 m in width.
- *Cultural requirements.*—Grow in full sun with moderate water and well-draining container medium or in well-draining sandy loam in the landscape.
- *Hardiness.*—USDA Zone 6.
- *Blooming season.*—Continually and repeat flowering from early summer into fall.

Stem (below first pinch):
- *Shape.*—Round.
- *Length.*—2 cm to 3 cm.
- *Diameter.*—8 mm.
- *Stem color.*—199B.
- *Texture.*—Slightly rough or coarse.

Branches:
- *Quantity.*—Approximately 50, of which 15 to 20 are primary branches and 30 or more are secondary branches.
- *Branching habit.*—Very freely branching, branches upright.
- *Branch shape.*—Round.
- *Length* (*to base of inflorescence*).—Primary branches 45 cm to 50 cm; secondary branches 30 cm to 35cm.
- *Diameter.*—7 mm (base of stem) to 3 mm (immediately below inflorescence).
- *Internode length.*—2.5 cm.
- *Color* (*juvenile growth*).—176B.
- *Color* (*mature growth*).—199B.
- *Surface.*—Slightly rough.
- *Strength.*—Stiff, firm.

Leaves:
- *Type, arrangement.*—Simple, alternate.
- *Attachment.*—Short petiolate.
- *Quantity.*—Approximately 30 leaves per branch and 1,500 to 1,800 leaves per plant.
- *Shape.*—Ovate.
- *Length.*—40 mm.
- *Width.*—22 mm.
- *Margin.*—Entire and colored with 178A.
- *Aspect.*—Outward facing, angled towards apex.
- *Texture* (*adaxial surface*).—Smooth, glabrous.
- *Texture* (*abaxial surface*).—Slightly rugose.
- *Color.*—Adaxial surface: 146A. Abaxial surface: 147B.
- *Apex.*—Rounded.
- *Base.*—Acute.
- *Venation.*—Pinnate.
- *Veins* (*adaxial surface*).—Color 185A.
- *Veins* (*abaxial surface*).—Color 145C, raised above leaf surface.

Petiole:
- *Shape.*—Cylindrical.
- *Length.*—1 mm.
- *Diameter.*—1 mm.
- *Color.*—147C.
- *Surface.*—Smooth.
- *Strength.*—Stiff and firm.

Peduncle:
- *Description.*—Branches from each stem, subtends paniculate inflorescence.
- *Shape.*—Cylindrical.
- *Length.*—4 cm.
- *Diameter.*—1.0 mm to 1.5 mm.
- *Texture.*—Smooth.
- *Color.*—183D.

Inflorescence:
- *Type.*—Panicle.
- *Length.*—9.5 cm.
- *Width.*—7.5 cm.
- *Quantity of inflorescences per plant.*—About 54.
- *Lastingness of the inflorescence on the plant.*—Up to 3 weeks.

Pedicels:
- *Length.*—7 mm.
- *Diameter.*—1 mm.
- *Texture.*—Smooth.
- *Color.*—184A.

Calyx:
- *Shape.*—Campanulate.
- *Height.*—11 mm.
- *Diameter.*—8 mm.

Sepals:
- *Quantity.*—6.
- *Shape.*—Acutely triangular.
- *Length.*—4 mm.
- *Width at base.*—3 mm.

*Apex.*—Acute.
*Base.*—Obtuse.
*Margin.*—Entire.
*Texture* (*both surfaces*).—Smooth to slightly rugose.
*Color* (*both surfaces*).—182C.

Flowers:
*Quantity per inflorescence* (*average*).—23 buds and flowers.
*Quantity per plant.*—Approximately 700 buds and flowers.
*Shape.*—Obovate.
*Fragrance.*—None.
*Lastingness of flowers.*—One week, then self-cleaning.
*Flower depth.*—2.0 cm.
*Flower diameter.*—3.5 cm.

Bud:
*Shape.*—Rounded hexagonal pyramid.
*Dimensions.*—8 mm in height, 7 mm in diameter.
*Surface.*—Smooth.
*Color.*—59A.

Petals:
*Quantity.*—6.
*Arrangement.*—Free, rotate.
*Shape.*—Obovate.
*Length.*—11 mm.
*Width.*—14 mm.
*Apex.*—Rounded.
*Base.*—Reniform.
*Margin.*—Smooth, undulating.
*Color* (*both surfaces*).—58A or 61B, depending on age of the petals and time of day.
*Texture* (*both surfaces*).—Smooth, glabrous.

Reproductive organs:
*Stamens, filaments.*—Quantity: 36. Arrangement: Upright cluster. Length: 1 mm. Diameter: 1 mm. Color: 155D.
*Anthers.*—Shape: Sulcate. Length: 2 mm-3 mm. Width: 1.5 mm. Color: 13B.
*Pollen.*—Amount: Moderate. Color: 14B.
*Pistil.*—Quantity: 1. Dimensions: 7 mm in length, 2 mm in diameter.
*Stigma.*—Shape: Club shaped. Length: 1 mm. Diameter: 1 mm. Color: 147D.
*Style.*—Color: 185D. Length: 5.0 mm.
*Ovary.*—Shape: Globular. Diameter: 3 mm. Color: 161D.
*Seed.*—Quantity: 14. Shape: Ovoid. Color: 144B.

Pest susceptibility: Slightly susceptible to aphids (*Aphis gossypii*) and occasionally to whitefly (*Trialeurodes vaporariorum*). In common with *Lagerstroemia* in general, 'JBG 19013' may become infected with crape myrtle bark scale (*Acanthococcus lagerstroemiae*).

Disease susceptibility: Slight incidence of powdery mildew (*Erysiphacea* spp.)

Heat, humidity and drought tolerance: Very well adapted to heat, humidity and drought conditions.

COMPARISON WITH PARENTAL LINE AND KNOWN VARIETY

'JBG 19013' may be compared with the female parent variety, *Lagerstroemia* 'Ruby Prince' by plant size and habit. Whereas 'Ruby Prince' is an upright and open tree form of *Lagerstroemia*, 'JBG 19013' is a mounded dense and compact shrub form.

When 'JBG 19013' is compared to 'JBG 19101' (U.S. Plant Pat. No. 33,726), 'JBG 19013' has pink flowers, while 'JBG 19101' has red flowers. Additionally, the petals of 'JBG 19013' are larger than 'JBG 19101'.

I claim:

1. A new and distinct cultivar of *Lagerstroemia* plant named 'JBG 19013' as described and illustrated herein.

* * * * *